United States Patent [19]

Perrault

[11] 4,025,508
[45] May 24, 1977

[54] 6-(TRIFLUOROMETHYL)-BENZOTHIADIAZINES

[75] Inventor: Marcel Perrault, Paris, France

[73] Assignee: Serdex - Societe d'Etudes, de Recherches, de Diffusion et d'Exploitation, Puteaux, France

[22] Filed: July 26, 1974

[21] Appl. No.: 492,978

[30] Foreign Application Priority Data

Aug. 6, 1973  France .................. 73.28691

[52] U.S. Cl. .................. 260/243 D; 260/508; 260/543 R; 260/556 B; 424/246
[51] Int. Cl.² .................. C07D 285/24
[58] Field of Search .................. 260/243 D

[56] References Cited

UNITED STATES PATENTS 3,345,365  10/1967  Topliss et al. .................. 260/243 D
3,361,816  1/1968  Topliss et al. .................. 260/243 D

FOREIGN PATENTS OR APPLICATIONS

M4,279     8/1966  France .................. 260/243 D
1,063,102  3/1967  United Kingdom .................. 260/243 D
1,054,632  1/1967  United Kingdom .................. 260/243 D

OTHER PUBLICATIONS

Serdex, Chem. Abs. 82, 156395m (1975).
Topliss et al., III, J. Med. Chem. I, 269(1964).

Primary Examiner—Donald G. Daus
Assistant Examiner—Mark L. Berch

Attorney, Agent, or Firm—Young & Thompson

[57] ABSTRACT

This invention relates to 2H-1,2,4-benzothiadiazine-1,1-dioxides having the general formula:

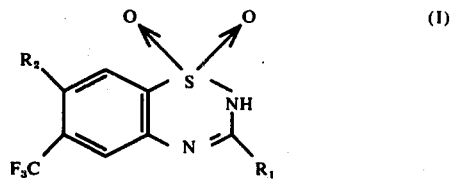

in which
  $R_1$ represents a hydrogen atom; an alkyl radical having 10–18 carbon atoms; an alkyl radical having 1–6 carbon atoms carrying one or more radicals selected from the halogens, the aryl radicals optionally carrying a halogen or an alkoxy radical having 1–6 carbon atoms, and the unsaturated 5- or 6-membered heterocyclic radicals including as heteroatoms oxygen, sulfur and/or nitrogen atoms; a polycyclanic radical having 8–12 carbon atoms; an aryl radical optionally carrying an alkoxy radical having 1–6 carbon atoms; or an unsaturated 5- or 6-membered heterocyclic radical including as heteroatom an oxygen, sulfur and/or nitrogen atom, and
  $R_2$ represents a halogen atom selected from bromine, fluorine and chlorine.

3 Claims, No Drawings

6-(TRIFLUOROMETHYL)-BENZOTHIADIAZINES

This invention relates to new benzothiadiazine derivatives having hyperglycemia-producing properties.

Said new derivatives are 2H-1,2,4-benzothiadiazine 1,1-dioxides having the general formula:

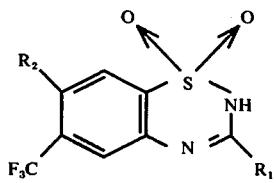

in which:

$R_1$ represents a hydrogen atom,
   an alkyl radical having 10–18 carbon atoms,
   an alkyl radical having 1–6 carbon atoms, carrying one or more radicals selected from the halogen atoms, the aryl radicals optionally carrying a halogen atom or an alkoxy radical having 1–6 carbon atoms, and the unsaturated 5- or 6-membered heterocyclic radicals including, as heteroatoms, oxygen, sulfur and/or nitrogen atoms,
   a polycyclanic radical having 8–12 carbon atoms,
   an aryl radical optionally carrying an alkoxy radical having 1–6 carbon atoms, or
   an unsaturated 5- or 6-membered heterocyclic radical including as heteroatom an oxygen, sulfur and/or nitrogen atom, and $R_2$ represents a halogen atom selected from bromine, fluorine and chlorine, and their pharmaceutically acceptable salts.

In the above definition, $R_1$ is typically: hydrogen; an alkyl radical having 10–18 carbon atoms; an alkyl radical having 1–3 carbon atoms, carrying one or two phenyl radicals which may optionally carry a halogen atom, a naphthyl radical or an indolyl radical; a polycyclanic radical having 8–12 carbon atoms; a phenyl radical optionally carrying a methoxy radical; or a heterocyclic radical selected from the pyridyl, thienyl and furyl radicals.

The compounds of this invention may be prepared by reacting an o-amino-sulfonamide of the formula (V)

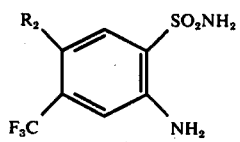

in which $R_2$ has the above-defined meaning, with an acylating agent having the formula

in which Z represents the hydroxy group, chlorine or the radical

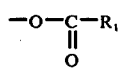

and $R_1$ has the above-defined meaning, to give a 2-acylamino-4-trifluoromethyl-5-halo-benzene sulfonamide having the formula

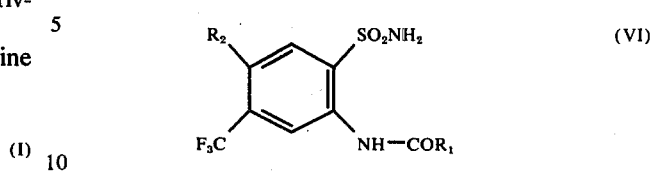

The acylamine of the formula (VI) is then cyclized to the corresponding 6-trifluoromethyl-7-halo-2H-1,2,4-benzothiadiazine-1,1-dioxide (I), in a variable monomer according to the nature of $R_1$ (thermal cyclization or cyclization in basic medium); the various cases will be mentioned in the Examples described hereinafter;

o-Aminosulfonamide (V) in which $R_2$ is a chlorine atom in a known compound (J. G. TOPLISS, L. M. KONZELMAN, E. P. SHAPIRO, N. SPERBER & F. E. ROTH, J. Med. Chem., 7, 269 (1964).

Generally, the compounds of the formula (V) may be prepared according to the following novel process: A 3-trifluoromethyl-4-halo-aniline (II) is sulfonated with chlorosulfonic acid and the resulting sulfonic acid (III) is converted to the chloride (IV) under the combined action of chlorosulfonic acid and thionyl chloride. The sulfonyl chloride (IV) produced is treated with concentrated ammonia to give 2-amino-4-trifluoromethyl-5-halobenzene-sulfonamide (V). The reaction sequence is summarized in the following scheme:

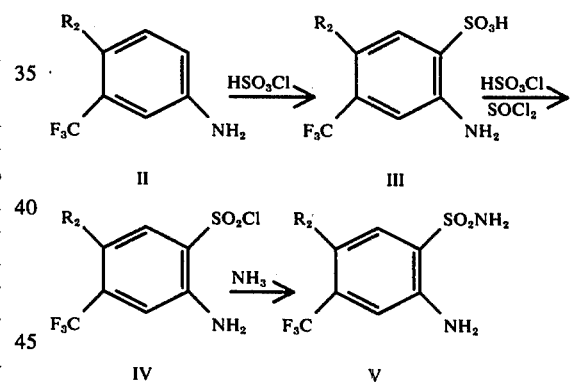

In the particular case of unsubstituted benzothiadiazine (formula I in which $R_1 = H$), the o-amino-benzene sulfonamide (V) may be reacted either with an orthoformate, in which case cyclization occurs simultaneously, or formic acid, as illustrated in the following Example:

EXAMPLE I 6-trifluoromethyl-7-fluoro-2H-1,2,4-benzothiadiazine-1,1-dioxide (formula I: $R_1 = H$; $R_2 = F$)

A. Action of ethyl orthoformate

A mixture of 6 g 2-amino-4-trifluoromethyl-5-fluoro-benzenesulfonamide, m.p. = 152° C (formula V: $R_2 =$ F) and 18 g ethyl orthoformate is heated at 120°–125° C, during 30 minutes to 1 hour, in an open vessel. After cooling, the reaction mixture is diluted with 150 ml dry diethyl ether. The resulting precipitate is collected and recrystallized from aqueous ethanol, to give 5.7 g of 6-trifluoromethyl-7-fluoro-2H-1,2,4-benzothiadiazine-1,1-dioxide, M.p = 234° C. B. Action of formic acid One part, by weight, aminobenzenesulfonamide (V) ($R_2 = F$) and three parts, by volume, formic acid are heated to the temperature of the boiling water-bath during 2 hours. The reaction medium is poured over 10 volumes water. The resulting precipitate is most frequently a mixture of benzothiadiazine and N-formyl-aminobenzene-sulfonamide (formula (VI): $R_1 = H$). It is sufficient to maintain this mixture at about 220° C for several minutes to achieve total cyclization. The crude reaction product is taken up into boiling benzene, after which it is filtered and recrystallized from aqueous ethanol, to give the desired benzothiadiazine. (Yield: 5.8 g from 6 g aminobenzene sulfonamide).

| Analysis: $C_8H_4F_4N_2O_2S$ (268.2) | C | H | N |
|---|---|---|---|
| Calculated %: | 35.82 | 1.50 | 10.44 |
| Found % : | 35.89 | 1.60 | 10.39 |

EXAMPLE 2

A. 2-Benzoylamino-4-trifluormethyl-5-fluoro-benzene sulfonamide (Formula (VI): $R_1 = F$)

6.5 g 2-amino-4-trifluoremethyl-5-fluoro-benzene sulfonamide are suspended in 150 ml dry benzene. 2.6 benzoyl chloride are added to the vigorously stirred suspension, after which the reaction mixture is gently refluxed during 4 hours. The reaction mixture is then left aside overnight. The resulting white solid is then suction filtered and recrystallized from aqueous ethanol, to give 6.1 g 2-benzoylamino-4-trifluoromethyl-5-fluoro-benzene sulfonamide, m.p. = 223° C.

| Analysis: $C_{14}H_{10}F_4N_2O_3S$ (362.4) | C | H | N |
|---|---|---|---|
| Calculated %: | 46.40 | 2.80 | 7.73 |
| Found %: | 46.46 | 2.74 | 7.92 |

B. 3-Phenyl-6-trifluoromethyl-7-fluoro-2H-1,2,4-benzothiadiazine-1,1-dioxide (Formula (I): $R_1 = $ phenyl; $R_2 = F$)

6 g of the compound prepared as in Example 2A are heated to 240°–250° C during 30–40 minutes. After cooling, the reaction mixture is taken up into 150 ml boiling benzene, the insoluble is filtered off and recrystallized from ethanol, to give 3.6 g of pearly flakes melting at 390° C.

| Analysis: $C_{14}H_8F_4N_2O_2S$ (344.3) | C | H | N |
|---|---|---|---|
| Calculated %: | 48.84 | 2.34 | 8.14 |
| Found %: | 48.72 | 2.40 | 8.12 |

EXAMPLE 3

A. 2-(1-Adamantyl-carbonylamino)-4-trifluoromethyl-5-fluorobenzene sulfonamide (formula (VI): $R_1 = $ 1-adamantyl; $R_2 = F$). Obtained as in Example 2A. M.p. = 211° C.
Yield: 5.8 g from 5.16 g aminobenzenesulfonamide.

| Analysis: $C_{18}H_{20}F_4N_2O_3S$ (420.4) | C | H | N |
|---|---|---|---|
| Calculated %: | 51.42 | 4.80 | 6.66 |
| Found %: | 51.15 | 4.64 | 6.51 |

B. 3-(1-Adamantyl)-6-trifluoromethyl-7-fluoro-2H-1,2,4-benzothiadiazine-1,1-dioxide (Formula (I): $R_1 = $ 1-adamantyl $R_2 = F$)

A solution of 5 g of the compound prepared according to Example 3A, 1 g caustic soda and 200 ml distilled water is gently boiled during one hour. After cooling, the reaction medium is made acidic with dilute hydrochloric acid. The resulting white precipitate is separated, thoroughly washed with water and recrystallized from aqueous ethanol, to give 3.4 g of the title benzothiadiazine, M.p. = 380° C.

| Analysis: $C_{18}H_{18}F_4N_2O_2S$ (402.4) | C | H | N |
|---|---|---|---|
| Calculated %: | 53.72 | 4.51 | 6.96 |
| Found %: | 53.65 | 4.44 | 7.17 |

EXAMPLE 4

A. 2-(3-Indolyl-acetylamino)-4-trifluoromethyl-5-fluorobenzenesulfonamide (Formula (VI): $R_1 = $ 3-indolyl-methyl; $R_2 = F$) M.p. = 228° C.

The procedure described in Example 2A gives 3 g of the above derivative from 4 g aminobenzene sulfonamide (V).

| Analysis: $C_{17}H_{13}F_4N_2O_3S$ (415.4) | C | H | N |
|---|---|---|---|
| Calculated %: | 49.16 | 3.16 | 10.12 |
| Found %: | 49.08 | 3.23 | 10.30 |

B. 3-(3-Indolyl-methyl)-6-trifluoromethyl-7-fluoro-2H-1,2,4-benzothiadiazine-1,1-dioxide (Formula (I): $R_1 = $ 3-indolyl-methyl $R_2 = F$)

The preceding derivative (2.2 g) is cyclized as in Example 3B, to give 1.7 g benzothiadiazine, M.p. = 314° C.

| Analysis: $C_{17}H_{11}F_4N_2O_2S$ (397.4) | C | H | N |
|---|---|---|---|
| Calculated %: | 51.39 | 2.79 | 10.59 |
| Found %: | 51.54 | 2.91 | 10.85 |

EXAMPLE 5

A. 2-p-Anisoylamino-4-trifluoromethyl-5-bromo-benzene sulfonamide (Formula (VI): $R_1 = $ p-methoxy phenyl; $R_2 = Br$)

2-Amino-4-trifluoromethyl-5-bromo-benzenesulfonamide (formula (V): $R_2 = Br$) is first prepared according to the above-described technique, M.p. = 202° C. The 2-amino-4-trifluoromethyl-5-bromobenzenesulfonamide (9.60 g) is then reacted, as in Example 2A, with p-anisic acid chloride (6.8 g), to give 12.2 g 2-p-anisoylamino-4-trifluoromethyl-5-bromo-benzenesulfonamide, M.p. = 321° C.

| Analysis: $C_{15}H_{12}BrF_3N_2O_4S$ (453.24) | C | H | N |
|---|---|---|---|
| Calculated %: | 39.74 | 6.18 | 7.07 |
| Found %: | 39.51 | 6.21 | 6.91 |

B.
3-(p-Methoxy-phenyl)-6-trifluoromethyl-7-bromo-2H-1,2,4-benzothiadiazine-1,1-dioxide (Formula (I): $R_1$ = p-methoxy-phenyl, $R_2$ = Br)

The p-anisoylaminobenzenesulfonamide prepared above (11 g) is dissolved in 200 ml 28% ammonia. The solution is heated during one hour at 70°–80° C and excess ammonia is then evaporated off. The residue is recrystallized from aqueous ethanol. M.p. = 382° C. Yield: 7.5 g.

| Analysis: $C_{15}H_{10}BrF_3N_2O_3S$ (435.23) | C | H | N |
|---|---|---|---|
| Calculated %: | 41.39 | 6.42 | 7.36 |
| Found %: | 41.18 | 6.12 | 7.13 |

EXAMPLE 6

A.
2-Nicotinoylamino-4-trifluoromethyl-5-chloro-benzenesulfonamide (Formula (VI): $R_1$ = 3-pyridyl; $R_2$ = Cl)

Obtained as described in Example 2A. M.p. = 223° C (free base). Yield = 10.5 g of base from 8.2 g aminotrifluoromethylchlorobenzenesulfonamide.

| Analysis: $C_{13}H_9ClF_3N_3O_3S$ (379.8) | C | H | N |
|---|---|---|---|
| Calculated %: | 41.11 | 2.39 | 11.07 |
| Found %: | 41.39 | 2.49 | 11.21 |

B.
3-(3-Pyridyl)-6-trifluoromethyl-7-chloro-2H-1,2,4-benzothiadiazine-1,1-dioxide (Formula (I): $R_1$ = 3-pyridyl; $R_2$ = Cl)

The cyclization of the above nicotinoyl derivative (11 g) in ammonia medium conducted as in Example 5B, gives 8.5 g of the benzothiadiazine. M.p. = 412° C (free base)

| Analysis: $C_{13}H_7ClF_3N_3O_2S$ (361.75) | C | H | N |
|---|---|---|---|
| Calculated % | 43.16 | 1.95 | 11.62 |
| Found % | 43.22 | 2.00 | 11.76 |

Further examples of compounds of the formula (I) according to the present invention are given below.

| Example | $R_1$ | $R_2$ | M.p. °C | C% Calc. | C% Found | H% Calc. | H% Found | N% Calc. | N% Found |
|---|---|---|---|---|---|---|---|---|---|
| 7 | Benzyl | F | 304 | 50.27 | 50.07 | 2.82 | 2.83 | 7.82 | 7.10 |
| 8 | 1-naphthyl methyl | F | 306 | 55.87 | 55.91 | 3.46 | 3.18 | 6.86 | 6.73 |
| 9 | 2-furyl | F | 360 | 43.11 | 43.22 | 1.81 | 1.92 | 8.38 | 8.09 |
| 10 | 3-chloro-benzyl | F | 267 | 45.80 | 45.66 | S% 8.17 | S% 8.01 | 7.14 | 7.38 |
| 11 | diphenylmethyl | F | 286 | 58.05 | 57.82 | 3.24 | 3.19 | 6.45 | 6.66 |
| 12 | benzyl | Br | 274 | 42.92 | 43.17 | 2.40 | 2.51 | 6.68 | 6.83 |
| 13 | 2-thienyl | F | 390 | 41.14 | 41.05 | | | 7.99 | 8.21 |
| 14 | pentadecanyl | F | 215 | 57.72 | 58.00 | 7.16 | 7.31 | 5.85 | 6.04 |
| 15 | 1-phenyl-1-propyl | F | 174 | 52.84 | 52.79 | 3.66 | 3.72 | 7.26 | 7.22 |
| 16 | p-methoxyphenyl | Cl | 388 | 46.09 | 45.80 | 2.57 | 2.73 | 7.17 | 7.20 |
| 17 | H | Cl | 269 | 33.76 | 33.65 | 1.42 | 1.54 | 9.87 | 9.90 |

Results of pharmacological tests demonstrating the pancreatotropic — particularly hyperglycemia-producing — activity and the low toxicity of the compounds of this invention are given below.

The following test methods were used to determine the hyperglycemia-producing activity:

a. Tests in Rats

The experiments were conducted in adult white rats weighing 200 g + 10 g.

The products were administered as a suspension in gummy julep, by stomach tube, at dosages of 10, 20 and 100 mg/kg, p.o.

At each dosage level, and in each case, lots of 10 test animals (5 male and 5 female) and of 10 reference animals (5 male and 5 female, administered only the gummy Julep) were used.

Blood samples were taken by cardiac puncture, at times 15, 60 minutes and 2, 4 and 24 hours after administration of the products, and the glycemia was determined.

b. Tests in Dogs

The investigations were carried out in dogs of various races, of either sex, weighing from 10 to 25 kg. The animals were anesthesized with chloralose (100 mg/kg i.v. ) and were submitted to artificial respiration.

The diastolic and systolic blood pressures were recorded with a Staham P23AA electromanometer, the cardiac rhythm was recorded with an OFFNER BECKMAN cardiotachometer and the electrocardiogram was recorded with a CARDIOLINE electrocardiograph. All parameters were recorded simultaneously on an eight-channel OFFNER BECKMAN dynograph apparatus.

The products, suspended in gummy Julep, were administered by the intraduodenal route at either 10 or 20, or at 100 mg/kg i.d. Blood samples were taken prior to the test, and then every hour during the 5 hours following administration of the products. Glycemia was determind.

The cardiovascular parameters were determined and calculated prior to the tests, and then after 2 minutes, 10 minutes, 30 minutes, 60 minutes, 1 hour, 2 hours, 3 hours, 4 hours, and 5 hours after administration of the products.

Under the experimental conditions adopted, the compounds prepared according to this invention were found to possess a hyperglycemia - producing activity. This activity was apparent both in rats and in dogs; it is low at 10 and 20 mg/kg, p.o.; it is highly significant at 100 mg/kg, p.o. The hyperglycemia-producing activity of the compounds is free from any concomitant hypotensive activity.

In addition, the compounds of this invention have low toxicity; their $LD_{50}/24$ hours is greater than 2–3 g/kg, p.o.

For illustrative purposes, the results obtained with the compound of Example 1 are given below.

The compound has no significant action on the glycemia of rats or dogs at 10 or 20 mg/kg, p.o.

At 100 mg/kg, p.o., it increases the glycemia of rats from $0.763 \pm 0.032$ g/l to $0.0990 \pm 0.024$ g/l, 2 hours after its administration, and from $0.839 \pm 0.042$ g/l to $1.212 \pm 0.041$ g/l, 24 hours after its administration.

at 100 mg/kg, p.o., it increases the glycemia of dogs by a factor of about 25%; at this dosage level, it has no significant action on the systolic, diastolic, mean and differential pressures, nor on the cardiac rhythm.

The $LD_{50}/24$ hours is 3.232 g/kg p.o.

The compounds of this invention are therapeutically useful as hyperclycemia-producing agents in the treatment of all hyperinsulinism conditions (hypoglycemia), whether functional or resulting from an injury: major hypoglycemia (adenoma or adenocarcinoma of $\alpha$ type); functional hypoglycemia and hyperinsulinism of florid obesity and of pre-diabetic conditions.

The compounds according to this invention may be administered as therapeutic compositions containing a therapeutically effective quantity of active ingredient in admixture with a pharmaceutically acceptable carrier or excipient. Such compositions are preferably orally administrable compositions, such as capsules or tablets which contain preferably 20–50 mg active ingredient.

Examples of such therapeutic compositions are given below.

| Tablets or capsules | weak dosage | strong dosage |
|---|---|---|
| Active ingredient | 20 mg | 50 mg |
| Excipient : rice starch talc magnesium stearate | q.s. for one tablet or capsule. | |

Having now described my invention what I claim as new and desire to secure by Letters Patent is:

1. A compound selected from the group consisting of compounds having the formula

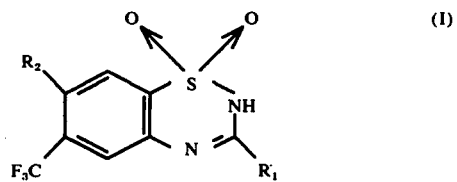

in which
$R_1$ is hydrogen;
and $R_2$ is selected from bromine, fluorine, and chlorine;
and a pharmaceutically acceptable salt thereof.

2. 6-Trifluoromethyl-7-fluoro-2H-1,2,4-benzothiadiazine-1,1-dioxide.

3. 6-Trifluoromethyl-7-chloro-2H-1,2,4-benzothiadiazine-1,1-dioxide.

* * * * *